(12) United States Patent
Arahira et al.

(10) Patent No.: US 6,372,469 B1
(45) Date of Patent: Apr. 16, 2002

(54) CDNA ENCODING PLANT-DERIVED EPOXIDE HYDROLASE, GENE ENCODING SAME AND TRANSFORMANT

(75) Inventors: Masaomi Arahira; Chikafusa Fukazawa, both of Tsukuba (JP)

(73) Assignee: Director of National Food Research Institute, Ministry of Agriculture, Forestry and Fisheries, Tsukuba (JP)

( * ) Notice: Subject to any disclaimer, the term of this patent is extended or adjusted under 35 U.S.C. 154(b) by 0 days.

(21) Appl. No.: 09/412,600

(22) Filed: Oct. 6, 1999

(30) Foreign Application Priority Data

Jan. 29, 1999 (JP) .............................. 11-021183

(51) Int. Cl.[7] .............................. C12N 9/12; C12N 1/20; C12N 15/00; C07H 21/04; C07K 1/00
(52) U.S. Cl. ................. 435/195; 435/252.3; 435/320.1; 530/350; 536/23.2
(58) Field of Search .............................. 435/195, 252.3, 435/320.1; 536/23.2; 530/350

(56) References Cited

PUBLICATIONS

Plant Physiol. 109, 722–723 (1995), Sep. 2, 1995.*
Sambrook et al.(1989), vol. 1, pp. 1.53–1.67, Sep. 2, 1995.*

* cited by examiner

*Primary Examiner*—Rebecca E. Prouty
*Assistant Examiner*—Tekchand Saidha
(74) *Attorney, Agent, or Firm*—Oblon, Spivak, McClelland, Maier & Neustadt, P.C.

(57) ABSTRACT

Isolation of a cDNA encoding a plant-derived epoxide hydrolase and an expression system of the enzyme in *Escherichia coli* are established, so as to permit the mass-scale production of the plant-derived epoxide hydrolase. The invention provides a cDNA encoding the plant-derived epoxide hydrolase having the amino acid sequence of SQ ID No. 1 in the Sequence Listing, a gene encoding the plant-derived epoxide hydrolase having the amino acid sequence of SQ ID No. 2 in the Sequence Listing, a plasmid vector carrying the cDNA and the transformant (FERM BP-6624) retaining the plasmid vector.

4 Claims, No Drawings

CDNA ENCODING PLANT-DERIVED EPOXIDE HYDROLASE, GENE ENCODING SAME AND TRANSFORMANT

FIELD OF THE INVENTION

The present invention relates to a cDNA encoding a plant-derived hydrolase, a gene encoding the same, a plasmid vector carrying said cDNA and a transformant.

BACKGROUND OF THE INVENTION

Epoxide hydrolase is an enzyme involved in the biological protective system functioning for preventing chemical reactions hazardous for living organisms in such a manner that the enzyme hydrolyses hazardous epoxide compounds generated through peroxidation in living organisms, to eliminate the high chemical reactivity of the epoxide compounds.

It is evidenced that epoxide hydrolase is present in animal cells and plant cells. Particularly, epoxide hydrolase derived from plants is expected to be applicable to agricultural fields and food industries. Because the content thereof is very low, the mass-scale production thereof has been believed to be extremely difficult.

As to genetic information concerning epoxide hydrolase, currently, reports have been issued about the genetic information thereof from animal cells, such as human liver cell [Beetham, J. K. et al., Arch. Biochem. Biophys., 305, 197–201 (1993)] and liver cells from rats and mice [Knehr, M. et al., J. Biol. Chem., 268, 17623–17627 (1993); Grant, D. F. et al., J. Biol. Chem., 268, 17628–17633 (1993)].

Meanwhile, the genetic information thereof from plant cells including potato [Stapleton, A. et al., Plant J. 6, 251–258 (1994)] and Arabidopsis [Kiyosue, T. et al., Plant J., 6, 259–269 (1994)] has been reported as well.

However, no report regarding genetic information about epoxide hydrolase derived from plants has been published yet, except the aforementioned reports. No plant-derived epoxide hydrolase with high activity has been reported yet.

SUMMARY OF THE INVENTION

The inventors have made attempts to purify a plant-derived epoxide hydrolase and to clone the cDNA and gene of the epoxide hydrolase based on the amino acid sequence thereof. Consequently, the inventors have successfully identified the whole structure of the cDNA of the enzyme and that of the gene thereof and have also achieved successfully the construction of an expression system in *Escherichia coli* by utilizing the cDNA and the gene. Thus, the invention has been achieved.

Based on the analysis of the amino acid sequence of the purified epoxide hydrolase, synthetic degenerate oligonucleotides were prepared. By subsequently extracting MRNA from a fully ripened soy seed and synthesizing a double-stranded cDNA using the mRNA, which was then integrated via an adapter into a phage vector, a cDNA library was constructed.

By labeling the prepared synthetic oligonucleotides and using the labeled synthetic oligonucleotides as probes, cDNA encoding the epoxide hydrolase of its full length was cloned by screening from the aforementioned cDNA library. The analysis of the primary structure of the cDNA indicated the whole amino acid sequence of the epoxide hydrolase including the signal peptide.

The epoxide hydrolase gene was cloned by using a commercially available gene library prepared by partially digesting nuclear DNA extracted and purified from sprout-developed soy with a restriction endonuclease Mbo I and integrating the digestion product in a phage vector.

By labeling the preliminarily recovered cDNA of the epoxide hydrolase and using the labeled cDNA as probe for screening from the aforementioned gene library, the epoxide hydrolase gene including the 5' upstream region was cloned.

Using the cloned epoxide hydrolase cDNA to construct an *Escherichia coli* expression system by utilizing a promoter $T_7$, the present enzyme was successfully expressed while a simple and rapid purification method thereof was also established.

More specifically, a first aspect of the invention relates to a cDNA encoding the plant-derived epoxide hydrolase having the amino acid sequence of SQ ID No. 1 in the Sequence Listing.

A second aspect of the invention relates to a gene encoding the plant-derived epoxide hydrolase having the amino acid sequence of SQ ID No. 2 in the Sequence Listing.

A third aspect of the invention relates to a plasmid vector carrying the cDNA encoding the plant-derived epoxide hydrolase in the first aspect of the invention.

A fourth aspect of the invention relates to a transformant (FERM BP-6624) retaining the plasmid vector in the third aspect of the invention.

DETAILED DESCRIPTION OF THE INVENTION

The invention will now be described in more detail hereinbelow.

As described in the column of "Description of the Related Art", the epoxide hydrolase of the invention is an enzyme with an action hydrolyzing epoxide hazardous to living organisms to generate diol and the like.

The first aspect of the invention is now described.

The first aspect of the invention relates to the cDNA encoding the plant-derived epoxide hydrolase having the amino acid sequence of SEQ ID No. 1 in the Sequence Listing.

The inventors have succeeded to obtain the cDNA of the first aspect of the invention in the following manner.

1. Preparation of cDNA Library 1.1 Extraction and Purification of Epoxide Hydrolase in Plants Epoxide hydrolase is present in cells of various plants and animals. In the first aspect of the invention, epoxide hydrolase derived from the cells of a plant is specifically used.

The cells of a plant are preferably cells of any seed with abundance of epoxide hydrolase, but are not limited thereto.

For extracting epoxide hydrolase from soy seed, use is preferably made of soy between early growing stage and ripe stage, preferably soy between early growing stage and later growing stage.

So as to obtain epoxide hydrolase, a raw material plant should necessarily be purified at a high level. The raw material plant includes for example soy, Arabidopsis, and potato.

The method for purifying the enzyme is illustrated in a case using soy as the raw material. Grinding the plant seed between early growing stage and ripe stage, and adding an appropriate buffer solution to the ground seed to extract the soluble fraction, the fraction is subjected to dialysis to separate the liquid fraction from the solid fraction. The resulting crude enzyme solution is applied to hydrophobic chromatography or gel filtration, whereby almost pure epoxide hydrolase can be recovered.

1.2 Analysis of Inner Amino Acid Sequence of Purified Epoxide Hydrolase

The purified epoxide hydrolase obtained in 1.1 cannot be analyzed as such of its inner amino acid sequence because the N terminus thereof is blocked. Therefore, the following procedures should be carried out.

Enzymatically degrading the epoxide hydrolase into short peptides and fractionating samples of the individual peptides by high performance liquid chromatography, the amino acid sequence of each of the samples is determined. The amino acid sequence is conveniently determined by Edman degradation using an automatic amino acid sequencer.

The individual samples are examined of their amino acid sequences; oligonucleotides are synthesized by using selected regions with less degeneracy among them; and the resulting oligonucleotides are used as the following probes.

1.3 Preparation of Poly(A)$^+$ RNA

RNA is then extracted from the plant seed, to prepare poly(A)$^+$ RNA from the extracted total RNA.

The poly (A)$^+$ RNA can be prepared from the plant by using the SDS-phenol method according to the method by Fukazawa, C. et al., Journal of Biological Chemistry, 200, 6234–6239 (1985).

1.4 Construction of cDNA Library

Synthetically preparing a double-stranded cDNA by using the resulting mRNA and integrating the cDNA via an adapter in a phage vector, a cDNA library is constructed.

The cDNA library can be prepared satisfactorily by various methods including for example the Okayama-Berg method [Okayama, H. and Berg, P., Mol. Cell Biol., 2, p. 161 (1982)] and the Gubler-Hoffman method [Gubler, U. and Hoffman, B. J., Gene, 25, p.263 (1983)]; and for simplicity, the latter method is preferable.

The Gubler-Hoffman method is now described below.

First, a double-stranded cDNA is synthetically prepared by using the poly(A)$^+$ RNA. To the cDNA is ligated an adapter carrying digestion sites with restriction endonucleases such as Eco RI, Not I and BamH I. By polyacrylamide gel electrophoresis, cDNAs of 500 bp or more are scissored out and collected from the gel, while excessive such adapter is removed.

Subsequently, a phosphate group is inserted at the 5' termini of the resulting nucleotide sequences, which are then restriction digested and ligated to the dephosphorylated λgt10 phage vector arm (manufactured by TaKaRa Brewery, Co.). The resulting nucleotide sequences are packaged in a λ phage. In such manner, a cDNA library is prepared.

2. Cloning of Plant-derived Epoxide Hydrolase cDNA of Full Length from cDNA Library and Determination of Nucleotide sequence thereof

2.1 Cloning of Full-length Epoxide Hydrolase cDNA

Labeling the oligonucleotides obtained above in 1.2 and using the resulting oligonucleotides as probes, the cloning of the plant-derived epoxide hydrolase cDNA of full length is accomplished by screening from the cDNA library described in 1.4.

The screening from the cDNA library is successfully executed by separating plaques positive at hybridization with plaques of about 1,000,000 in number, using, as probes, the radio-labeled synthetic oligonucleotides [Fukazawa, C. et al., Journal of Biological Chemistry, 200, 6234–6239 (1985)].

Purifying the resulting positive plaques and allowing *Escherichia coli* to be infected with the plaques to proliferate the phage, the phage particle is purified to obtain phage DNA. The phage DNA can be purified by ultra-filtration method on a CsCl step-wise density gradient.

2.2 Structure Determination of Recovered Phage DNA

From the purified phage DNA is cleaved the insert with a restriction enzyme, which is then purified. The insert is sub-cloned in a plasmid vector, for DNA sequencing. Consequently, the cDNA encoding the amino acid sequence of SEQ ID No. 1 in the Sequence Listing was obtained. The analysis of the cDNA suggested that the cDNA of the positive plaque cloned encoded the full-length epoxide hydrolase. More specifically, the cDNA is according to the first aspect of the invention.

The cDNA composed of 1,332 bp in its full length encodes 341 amino acids in total from the starting methionine.

The second aspect of the invention is now described.

The second aspect of the invention relates to the gene encoding the plant-derived epoxide hydrolase having the amino acid sequence of SEQ ID No:4 in the Sequence Listing.

The gene of the second aspect of the invention can be obtained on the basis of the cDNA of the first aspect of the invention. Continuously subsequent to the identification of the cDNA sequence in the first aspect of the invention, the inventors have selected the following steps.

3. Cloning of Plant-derived Epoxide Hydrolase Gene of Full Length and Determination of Nucleotide Sequence Thereof Through screening from a commercially available soy gene library (Stratagene Ltd.) using the labeled cDNA of the first aspect of the invention as probe, the cloning of the plant-derived epoxide hydrolase gene of its full length is accomplished. The cloning is successfully achieved through the aforementioned plaque hybridization, to subsequently select positive phages.

The soy gene library purchased from the commercial source has been prepared by extracting and purifying nuclear DNA from sprout-developed soy and partially digesting the nuclear DNA with a restriction endonuclease Mbo I, and thereafter integrating the digestion product in a phage vector.

Purifying the resulting positive phages and allowing the phages to be subcloned in a plasmid vector, the DNA was sequenced by the same method as described above in 2.2. Consequently, the nucleotide sequence of the plant-derived epoxide hydrolase gene and the amino acid sequence encoded thereby can be recovered in accordance with the second aspect of the invention (see SEQ ID No: 2 in the Sequence Listing).

The sequence is composed of 1,933 bp in its full length (see SEQ ID No: 3 in the Sequence Listing), wherein two introns divide the sequence into three exons.

The individual introns, namely first intron and second intron, are composed of 168 bp and 148 bp, respectively, in nucleotide number. (See SEQ ID No: 3 in the Sequence Listing.)

The third aspect and fourth aspect of the invention will now be described collectively.

The third aspect of the invention relates to a plasmid vector carrying the cDNA encoding the plant-derived epoxide hydrolase in the first aspect of the invention.

The fourth aspect of the invention relates to a transformant retaining the plasmid vector in the third aspect of the invention.

In other words, the third and fourth aspects of the invention provide an expression system of the plant-derived epoxide hydrolase.

The plasmid vector and transformant described in the third and fourth aspects, respectively, of the invention are prepared by the following procedures.

4. Preparation of Plasmid Vector and Transformant 4.1 PCR Amplification of cDNA Nucleotide Sequence in the First Aspect of the Invention Based on the cDNA nucleotide sequence in the first aspect of the invention (see SEQ ID No. 1 in the Sequence Listing) and the ion-spray mass spectrometry of the purified epoxide hydrolase, a 32-mer oligonucleotide primer containing a restriction Nde I site at the 5' terminus (N terminus) and a 34-mer oligonucleotide primer containing a restriction Eco RI site at the 5' terminus (C terminus), are synthesized (see SEQ ID Nos: 6 and 7 in the Sequence Listing). Restriction enzymes suitable for the expression vectors described below can satisfactorily be used, so the enzymes are not limited to the restriction enzymes described above.

PCR was conducted by using these primers and using the plant-derived epoxide hydrolase cDNA of the first aspect of the invention as template. PCR can be performed, for example, under the conditions described in Example 3, with no specific limitation.

4.2 Preparation of Plasmid Vector and Transformant

The band recovered in 4.1 was sub-cloned in a TA vector [pCR2.1] (manufactured by Invitrogen Co.) and was then subjected to DNA sequencing by the same method as described in 2.2, whereby it was confirmed that no mutation occurred in the expression cDNA amplified by PCR.

Additionally, the insert was cleaved out of the cloned TA vector by using restriction endonucleases Nde I and Eco RI contained in the aforementioned individual PCR primers, which was then purified; the resulting purified insert was sub-cloned in between the Nde I site and Eco RI site of the pRSET vector (manufactured by Invitrogen Co.) as expression plasmid. The resulting plasmid is a plasmid of the third aspect of the invention.

The plasmid of the third aspect of the invention is used for transformation of expression *Escherichia coli*, for example *Escherichia coli* BL21 (DE3) (manufactured by Novagen), to recover a transformant of the fourth aspect of the invention.

Transformation is conducted by general methods including for example calcium chloride method (Cohen, S. N., Chang, A. C. Y. and Hsu, L., Proc. Natl. Acad. Sci. USA, 69: 2110–2114, 1972) and electroporation method (New Experimental Methods For Fundamental Biochemistry, Kinichiro Miura et al. ed., Genetic Engineering, 1988, Maruzen).

The transformed *Escherichia coli* is deposited as Accession No. FERM BP-6624 at National Institute of Bioscience and Human Technology, Agency of Industrial Science and Technology (1–3, Higashi 1-chome, Tsukuba-shi, Ibaraki-ken, Japan).

By culturing the transformant *Escherichia coli* of the fourth aspect of the invention and identifying the amino acid sequence carried in the *Escherichia coli* or assaying the specific activity of the enzyme, the expression of the gene of the second aspect of the invention can be confirmed.

Not any plant-derived epoxide hydrolase with a high activity has been demonstrated insofar. The system for expressing such highly active plant-derived epoxide hydrolase at a mass scale is very useful for assessing the function of the enzyme gene in a simple manner.

According to the first and second aspects of the invention, the cDNA encoding the plant-derived epoxide hydrolase and the gene encoding the plant-derived epoxide hydrolase are provided. By using the cDNA and the gene, an epoxide hydrolase gene with significant functions for protecting biological organisms can readily be developed and may be applicable to plants for foods.

According to the third and fourth aspect of the invention, the plasmid vector carrying the cDNA encoding the plant-derived epoxide hydrolase and the transformant retaining the plasmid vector are provided. The transformant can be utilized effectively as an expression system in microorganisms for assessing the functions of the gene encoding the epoxide hydrolase simply and easily.

EXAMPLES

Example 1

Preparation of cDNA of Plant-derived Epoxide Hydrolase and Determination of Nucleotide Sequence Thereof 1. Preparation of cDNA Library From a soy seed on day 18 after blooming was extracted total RNA by the SDS-phenol method according to the method by Fukazawa, C. et al., Journal of Biological Chemistry, 200, 6234–6239 (1985), to prepare poly(A)$^+$ RNA.

A double-stranded DNA was synthetically prepared by using 2.5 $\mu$g of the poly(A)$^+$ RNA and a cDNA synthesis kit based on the principle of the Gubler-Hoffmann method (manufactured by Amersham-Pharmacia Co. Ltd.) while adding [$\alpha$-$^{32}$P]-dCTP for monitoring the synthesis thereof.

1 nmol of the Eco RI-Not I-Bam HI adapter (manufactured by TaKaRa Brewery, Co. Ltd.) was ligated to the resulting cDNA by using a ligation pack manufactured by Nippon Gene Co. Said cDNAs of 500 bp or longer were cleaved and collected out of the gel by polyacrylamide gel electrophoresis according to the method by Fukazawa, C. et al., Journal of Biological Chemistry, 200, 6234–6239 (1985), while an excess of the adapter was removed.

Because no phosphate group was present at the 5' terminus of the adapter, a phosphate group was introduced therein by using a T$_4$ nucleotide kinase (manufactured by Nippon Gene Co.)

Subsequently, the resulting cDNAs were digested with Eco RI and ligated to the dephosphorylated λgt10 phage vector arm (manufactured by TaKaRa Brewery, Co.) in the same manner as described above by using the ligation pack (manufactured by Nippon Gene Co.), for packaging into λ phage by using an in vitro packaging kit (manufactured by Amersham-Pharmacia Co.). In such manner, a cDNA library of ripened soy seed on day 18 after blooming was prepared.

2. Amino Acid Sequencing of Plant-derived Epoxide Hydrolase and Probe Preparation A soy seed on day 18 after blooming was ground, to which was added an acetate buffer. Then, asoluble fraction containing epoxide hydrolase was extracted and dialyzed; the resulting fraction was subjected to hydrophobic chromatography (column: Butyl Toyo-pearl of 5 c×90 cm; manufactured by Tosoh, Co. Ltd.) and subsequent gel filtration on a column Sephacryl S-200 of a size of 2.6 cm×180 cm; manufactured by Amersham-Pharmacia Co.), to recover nearly purified epoxide hydrolase.

The plant-derived epoxide hydrolase had the blocked N terminus. So as to determine the inner amino acid sequence, therefore, the epoxide hydrolase was degraded with V8 protease (manufactured by TaKaRa Brewery, Co.) and lysyl endopeptidase (manufactured by Wako Pure Chemicals, Co.) according to the method by Arahira M. and Fukazawa C., Plant Molecular Biology, 25, 597–605 (1994).

After degradation, individual samples were fractionated by an HPLC system (LC-6AD manufactured by Shimadzu, Co. Ltd.) in connection to a reverse-phase column (Silica ODS 120T of 4.6 mm×150 mm manufactured by Tosoh, Co. Ltd.) with an eluent on a linear 0.1% TFA–0.1% TFA/60% acetonitrile density gradient.

The amino acid sequences of the resulting peptides were assayed by a gas-phase amino acid sequencer (Type 477A manufactured by Perkin-Elmer Japan), which demonstrates the inner amino acid sequence of the epoxide hydrolase.

Among the amino acid sequences, a sequence suitable as probe was examined. A 23-mer degenerate oligonucleotide was synthesized (see SEQ ID No:5 in the Sequence Listing).

3. Cloning of plant-derived epoxide hydrolase cDNA

The oligonucleotide recovered above in 2 was labeled with $[\gamma^{-32}p]$-ATP according to the method by Fukawaza, C. et al., Journal of Biological Chemistry, 200, 6234–6239 (1985).

Using the oligonucleotide as probe and the library of a ripened soy seed on day 18 after blooming as prepared above in 1, plaque hybridization was carried out according to the method by Arahira M. and Fukazawa C., Plant Molecular Biology, 25, 597–605 (1994). Consequently, a single positive clone was isolated from 1,000,000 plaques.

*Escherichia coli* was infected with the positive plaque purified, to proliferate the phage; subsequently, the phage particle was purified by ultra-centrifugation on a CsCl step-wise density gradient, to recover phage DNA.

From the purified phage DNA was cleaved the insert with Bam HI; the insert was purified from the agarose gel and subcloned in the Ham HI site of a plasmid vector pUC19. From the cloned *Escherichia coli* was prepared the plasmid DNA by a routine method [Maniatis, T. et al., "Molecular Cloning", Cold Spring Harbor Labo. (1982)].

The prepared plasmid was subjected to fluorescence autosequencing using a DNA sequencer DSQ1000 manufactured by Shimadzu. The results of the analysis indicate that the cDNA of the positive cloned plaque contained the full-length epoxide hydrolase and was of the nucleotide sequence and amino acid sequence of SEQ ID No: 1 in the Sequence Listing.

The full-length cDNA was composed of 1,332 bp, where 22 bp composed poly A. The number of the total amino acids encoded by the cDNA was 341 from the starting methionine; based on the molecular weight (36171Da) analysis by ion-spray mass spectrometry, it was estimated that the amino acid sequence was composed of 315 amino acid residues.

Example 2

Cloning of Plant-derived Epoxide Hydrolase Gene

1. Cloning of Epoxide Hydrolase Gene

Using $[\alpha^{-32}P]$-dCTP, the cDNA recovered in Example 1 was labeled according to the method by Arahira M. and Fukazawa C., Plant Molecular Biology, 25, 597–605 (1994), which was used as probe.

By the same method as described in Example 1, Section 3, the epoxide hydrolase gene was screened from the commercially available soy gene library (manufactured by Stratagene Ltd.) with a use of said probe to recover a single positive plaque from about 200,000 plaques, to purify phage DNA.

The library purchased from the commercial manufacturer had been prepared by extracting and purifying nuclear DNA from a sprouted soy plant, which had been digested partially with a restriction endonuclease Mbo I to subsequently be integrated into a phage vector.

The positive phage DNA contained an insert of about 12 kbp. The insert was cleaved out with a restriction endonuclease Sal I and was then purified on agarose gel; the resulting insert was subcloned in a plasmid vector pUC19. Subsequently, DNA sequencing was carried out by the method described in Example 1, Section 3. The results of the sequencing indicate that the cloned gene was of the nucleotide sequence and amino acid sequence in SEQ ID No: 3 in the Sequence Listing.

The full-length sequence was composed of 1,933 bp, which was divided by two introns into three exons. The numbers of nucleotides in the first and second introns were 168 bp and 148 bp, respectively (see SEQ ID No. 3 in the Sequence Listing).

The nucleotide sequence of the gene of the resulting soy epoxidehydrolase was analyzed with reference to database. The results indicate that the nucleotide sequence was different from any nucleotide sequence of cDNAs elucidated for Arabidopsis and potato. Thus, the nucleotide sequence was a novel genetic sequence in plants.

Example 3

Expression of Plant-derived Epoxide Hydrolase in *Escherichia coli*

1. PCR Amplification of Epoxide Hydrolase cDNA

Preparing first individual primers containing restriction sites required for constructing an expression plasmid in *Escherichia coli* at the 5' terminus (see SEQ ID No:6 and 7 in the Sequence Listing) respectively for the N-terminus side of a protein speculated on the basis of the molecular weight of the epoxide hydrolase as determined by ion-spray mass spectrometry and for the side of the stop codon of the epoxide hydrolase cDNA (C-terminus side of the epoxide hydrolase protein), PCR was carried out, using as template the plant-derived epoxide hydrolase cDNA cloned in Example 1.

PCR conditions are as follows.

First, 2.5 U of Taq polymerase TaKaRa ExTaq (manufactured by TaKaRa Brewery, Co.) was used per one reaction. Furthermore, the primers were used at a final concentration of 0.4 $\mu$M; DNTP mix was at 0.2 mM; and the template epoxide hydrolase cDNA fragment was used at about 10 ng.

TaKaRa PCR thermal cycler 480 (manufactured by TaKaRa Brewery, Co.) was used as a gene amplification system for carrying out 35 cycles of amplification using a step program as follows; 95° C. for 30 seconds for denaturation step, 56° C. for 30 seconds for annealing step and 72° C. for 1.5 minutes for extension step.

The resulting band was subcloned in a TA vector [PCR2.1] (manufactured by Invitrogen Co.). Subsequently, DNA sequencing was carried out by the method described in Example 1, Section 3. The results of the analysis indicate no observed mutation due to PCR.

2. Preparation of Plasmid Vector and Transformant

Cleaving the insert out of the cloned TA vector with the restriction endonucleases Nde I and Eco RI contained in the individual primers, then, the resulting DNA fragment was purified on agarose gel and subcloned between the Nde I site and the Eco RI site of an expression plasmid pRSET vector (manufactured by Invitrogen Co.).

So as to examine whether or not the DNA sequence at the part connecting the insert epoxide hydrolase cDNA fragment and the PRSET vector was accurate, the subcloned DNA fragment was used for transformation of an *Escherichia coli* strain JM109 with no protein expression ability although the strain carried an expression plasmid. This is because if an expressed protein might be toxic to *Escherichia coli*, said *Escherichia coli* could be damaged by a slight expression of the expression plasmid resulting in hindering the DNA extraction, etc.

By the method described in Example 1, [3], DNA sequencing was carried out. The results of the analysis indicate that the connection part was accurately sequenced.

An expression *Escherichia coli* strain BL21 (DE3) was transformed with the expression plasmid. The *Escherichia coli* strain thus transformed is deposited at National Institute of Bioscience and Human Technology, Agency of Industrial Science and Technology (1–3, Higashi 1-chome, Tsukuba-shi, Ibaraki-ken, Japan), under Accession No. FERM BP-6624.

Example 4

Expression of Epoxide Hydrolase From Transformant

Then, the expression *Escherichia coli* strain BL21 (DE3) transformed with the expression plasmid was allowed to express the epoxide hydrolase. A single colony was first inoculated on a culture medium of 2-ml LB/ampicillin (at a concentration of 50 µg/ml), which was then cultured under agitation at 37° C. and 200 rpm overnight, which was used as pre-culture.

One liter of the culture medium was placed in a 5-liter Erlenmeyer flask, into which 1 ml of the pre-cultured bacteria solution was inoculated and cultured at 37° C. and 200 rpm, until the OD at 600 nm reached about 0.6. Just when the OD at 600 nm reached about 0.6, isopropyl β-D-thiogalactopyranoside (IPTG) was added to the culture to a final concentration of 1 mM, for culturing for additional 3 hours under the aforementioned conditions.

After termination of the culturing, the culture was centrifuged to harvest the bacteria; the bacteria were washed with 200 mM acetate buffer, pH 5.0 containing 100 mM NaCl and 1 mM EDTA and was then suspended in the same buffer; then, the bacteria in the resulting suspension were disrupted by ultrasonic treatment, to recover the supernatant.

The resulting supernatant was thermally treated at 55° C. for 10 minutes, to denature most of the protein derived from *Escherichia coli*, which was then separated by centrifugation.

Most of the resulting supernatant protein was epoxide hydrolase expressed, which was further purified.

The supernatant was subjected to and fractionated by gel filtration on a Sephacryl S-200 column (2.6×90 cm) (manufactured by Amersham-Pharmacia Co.). The resulting fraction was at a single band on SDS-PAGE. The N-terminal sequence of the protein was determined by a gas-phase amino acid sequencer (Type 477A; manufactured by Perkin-Elmer) in the same manner as in Example 1, Section 2. It was confirmed that the protein was epoxide hydrolase.

The resulting soy-derived epoxide hydrolase was of a molecular weight of 33 kDa (as a single band) on SDS-PAGE and with a specific activity of 1.36U/mg (1 U=1 µmol/min) to styrene oxide.

As has been described above, it is shown that the purified enzyme had a high enzyme activity and exerts an excellent ability to hydrolyze hazardous epoxide to modify the epoxide into non-hazardous materials.

What is claimed is:

1. A plasmid DNA comprising an amplified DNA product wherein said amplified DNA product is obtained by amplifying a soybean seed-derived epoxide hydrolase cDNA comprising SEQ ID NO:1 with oligonucleotide primers SEQ ID NO:6 and SEQ ID NO:7, wherein said plasmid DNA expresses an epoxide hydrolase.

2. A host cell comprising the plasmid DNA claim 1.

3. The host cell of claim 2, which is FERM BP-6624.

4. A method of expressing epoxide hydrolase comprising amplifying SEQ ID NO:1 with primers comprising the sequences in SEQ ID NO:6 and SEQ ID NO:7 to produce an amplified epoxide hydrolase polynucleotide;

inserting said amplified epoxide hydrolase polynucleotide in a plasmid vector;

transforming a host cell with said plasmid vector;

culturing said host cell in a culture medium to express the protein encoded by said amplified epoxide hydrolase polynucleotide; and recovering said epoxide hydrolase.

* * * * *

UNITED STATES PATENT AND TRADEMARK OFFICE
CERTIFICATE OF CORRECTION

PATENT NO.    : 6,372,469 B1
DATED         : April 16, 2002
INVENTOR(S)   : Arahira et al.

It is certified that error appears in the above-identified patent and that said Letters Patent is hereby corrected as shown below:

<u>Title page,</u>
Item [45] and the Notice information should read as follows:

-- [45] Date of Patent:  *Apr. 16, 2002

[*]  Notice:  This patent issued on a continued prosecution application filed under 37 CFR 1.53(d), and is subject to the twenty year patent term provisions of 35 U.S.C 154(a)(2).

Subject to any disclaimer, the term of this patent is extended or adjusted under 35 U.S.C 154(b) by 0 days. --

Signed and Sealed this

Fourth Day of February, 2003

JAMES E. ROGAN
*Director of the United States Patent and Trademark Office*

SEQUENCE LISTING

```
<160> NUMBER OF SEQ ID NOS: 7

<210> SEQ ID NO 1
<211> LENGTH: 1332
<212> TYPE: DNA
<213> ORGANISM: Glycine max
<220> FEATURE:
<221> NAME/KEY: CDS
<222> LOCATION: (73)..(1098)

<400> SEQUENCE: 1
gaggagccta cggtttggca ttgagtgtga aacaggctaa taaatgtgag tggttcaccg       60
ccgcaacttc ca atg tgc gag cac tta ctc gtc tca ctg tct tgc tat att      111
              Met Cys Glu His Leu Leu Val Ser Leu Ser Cys Tyr Ile
                1               5                  10 tgg gtg aga aca cag agg ata gtg gag ttc aac gag atg gag caa ata        159
Trp Val Arg Thr Gln Arg Ile Val Glu Phe Asn Glu Met Glu Gln Ile
 15                  20                  25 agg cac aga aca gtt gaa gtg aat ggc ata aaa atg cat gtt gca gag        207
Arg His Arg Thr Val Glu Val Asn Gly Ile Lys Met His Val Ala Glu
 30                  35                  40                  45 aaa gga gag ggt cca gtg gtg ttg ttc ctc cac ggc ttc cct gag ctc        255
Lys Gly Glu Gly Pro Val Val Leu Phe Leu His Gly Phe Pro Glu Leu
                 50                  55                  60 tgg tac tca tgg cgc cat cag att ctc tct ctc agc tcc ctc ggc tac        303
Trp Tyr Ser Trp Arg His Gln Ile Leu Ser Leu Ser Ser Leu Gly Tyr
             65                  70                  75 cgc gcc gtc gct ccc gat ctc cgt ggc tac ggt gac acc gag gca cca        351
Arg Ala Val Ala Pro Asp Leu Arg Gly Tyr Gly Asp Thr Glu Ala Pro
         80                  85                  90
```

```
cct tca atc agc agc tac aac tgc ttc cac ata gtg ggt gat ctc gtt         399
Pro Ser Ile Ser Ser Tyr Asn Cys Phe His Ile Val Gly Asp Leu Val
     95                 100                 105 gcg ctt att gac tct ctg ggt gtc caa caa gtg ttc ctt gtg gct cat         447
Ala Leu Ile Asp Ser Leu Gly Val Gln Gln Val Phe Leu Val Ala His
110                 115                 120                 125 gac tgg gga gcc atc ata ggt tgg tat cta tgc atg ttt cgc cct gac         495
Asp Trp Gly Ala Ile Ile Gly Trp Tyr Leu Cys Met Phe Arg Pro Asp
                    130                 135                 140 aaa gtt aag gcc tat gtc tgc ctc agt gtc cct ctc ctc cgc aga gac         543
Lys Val Lys Ala Tyr Val Cys Leu Ser Val Pro Leu Leu Arg Arg Asp
                145                 150                 155 cca aac atc aga acg gtg gat ggc atg cgt gct ttg tat gga gac gac         591
Pro Asn Ile Arg Thr Val Asp Gly Met Arg Ala Leu Tyr Gly Asp Asp
            160                 165                 170 tac tat gtc tgc aga ttt cag aaa cca ggg gaa atg gag gct cag atg         639
Tyr Tyr Val Cys Arg Phe Gln Lys Pro Gly Glu Met Glu Ala Gln Met
    175                 180                 185 gct gaa gtt ggc act gag tat gtt ctc aaa aac atc ctt aca act cgc         687
Ala Glu Val Gly Thr Glu Tyr Val Leu Lys Asn Ile Leu Thr Thr Arg
190                 195                 200                 205 aat cct ggt cct cca att ctt ccc aag gga agg ttt caa ttc aat cca         735
Asn Pro Gly Pro Pro Ile Leu Pro Lys Gly Arg Phe Gln Phe Asn Pro
                    210                 215                 220 gaa atg ccc aac acc ttg ccc tct tgg ctc aca gaa gaa gat ctc gcc         783
Glu Met Pro Asn Thr Leu Pro Ser Trp Leu Thr Glu Glu Asp Leu Ala
                225                 230                 235 tat tat gtc tcc aaa ttt gag aaa acc gga ttc act gga ccc ttg aac         831
Tyr Tyr Val Ser Lys Phe Glu Lys Thr Gly Phe Thr Gly Pro Leu Asn
            240                 245                 250 tac tac aga aat ttc aac tta aat tgg gag ttg acg gca cca tgg aca         879
Tyr Tyr Arg Asn Phe Asn Leu Asn Trp Glu Leu Thr Ala Pro Trp Thr
    255                 260                 265 gga ggg cca atc aag gtg ccc gta aaa tac ata aca ggt gag ttg gac         927
Gly Gly Pro Ile Lys Val Pro Val Lys Tyr Ile Thr Gly Glu Leu Asp
270                 275                 280                 285 atg gta tac aac tcg ctg aac ttg aag gag tat atc cac ggc gga ggg         975
Met Val Tyr Asn Ser Leu Asn Leu Lys Glu Tyr Ile His Gly Gly Gly
                    290                 295                 300 ttc aag caa gat gtg cca aat tta gaa caa gtg att gtg cag aaa gga        1023
Phe Lys Gln Asp Val Pro Asn Leu Glu Gln Val Ile Val Gln Lys Gly
                305                 310                 315 gtg gct cac ttc aat aat caa gaa gca gca gag gaa atc gat aat tac        1071
Val Ala His Phe Asn Asn Gln Glu Ala Ala Glu Glu Ile Asp Asn Tyr
            320                 325                 330 ata tac gat ttt atc aaa aag ttc tga tcttgtccaa aaacgaattc              1118
Ile Tyr Asp Phe Ile Lys Lys Phe
    335                 340 aaccagatat aaagtcgcag ctgaagtgaa agggtgttat aattgcgctt ttgttttgat     1178
atttaaggta tcgagatctt ttttatgggc aggattcatc aactgcagaa aacctccata     1238
ccatcaacct tcctatgcct gtttgtatta attaactgat aataatactg tatggtttgg     1298
tacttgctaa ataaaaaaaa aaaaaaaaaa aaaa                                 1332

<210> SEQ ID NO 2
<211> LENGTH: 341
<212> TYPE: PRT
<213> ORGANISM: Glycine max
```

```
<400> SEQUENCE: 2

Met Cys Glu His Leu Leu Val Ser Leu Ser Cys Tyr Ile Trp Val Arg
 1               5                  10                  15

Thr Gln Arg Ile Val Glu Phe Asn Glu Met Glu Gln Ile Arg His Arg
            20                  25                  30

Thr Val Glu Val Asn Gly Ile Lys Met His Val Ala Glu Lys Gly Glu
        35                  40                  45

Gly Pro Val Val Leu Phe Leu His Gly Phe Pro Glu Leu Trp Tyr Ser
    50                  55                  60

Trp Arg His Gln Ile Leu Ser Leu Ser Ser Leu Gly Tyr Arg Ala Val
 65                  70                  75                  80

Ala Pro Asp Leu Arg Gly Tyr Gly Asp Thr Glu Ala Pro Pro Ser Ile
                85                  90                  95

Ser Ser Tyr Asn Cys Phe His Ile Val Gly Asp Leu Val Ala Leu Ile
            100                 105                 110

Asp Ser Leu Gly Val Gln Gln Val Phe Leu Val Ala His Asp Trp Gly
        115                 120                 125

Ala Ile Ile Gly Trp Tyr Leu Cys Met Phe Arg Pro Asp Lys Val Lys
    130                 135                 140

Ala Tyr Val Cys Leu Ser Val Pro Leu Leu Arg Arg Asp Pro Asn Ile
145                 150                 155                 160

Arg Thr Val Asp Gly Met Arg Ala Leu Tyr Gly Asp Asp Tyr Tyr Val
                165                 170                 175

Cys Arg Phe Gln Lys Pro Gly Glu Met Glu Ala Gln Met Ala Glu Val
            180                 185                 190

Gly Thr Glu Tyr Val Leu Lys Asn Ile Leu Thr Thr Arg Asn Pro Gly
        195                 200                 205

Pro Pro Ile Leu Pro Lys Gly Arg Phe Gln Phe Asn Pro Glu Met Pro
    210                 215                 220

Asn Thr Leu Pro Ser Trp Leu Thr Glu Glu Asp Leu Ala Tyr Tyr Val
225                 230                 235                 240

Ser Lys Phe Glu Lys Thr Gly Phe Thr Gly Pro Leu Asn Tyr Tyr Arg
                245                 250                 255

Asn Phe Asn Leu Asn Trp Glu Leu Thr Ala Pro Trp Thr Gly Gly Pro
            260                 265                 270

Ile Lys Val Pro Val Lys Tyr Ile Thr Gly Glu Leu Asp Met Val Tyr
        275                 280                 285

Asn Ser Leu Asn Leu Lys Glu Tyr Ile His Gly Gly Phe Lys Gln
    290                 295                 300

Asp Val Pro Asn Leu Glu Gln Val Ile Val Gln Lys Gly Val Ala His
305                 310                 315                 320

Phe Asn Asn Gln Glu Ala Ala Glu Glu Ile Asp Asn Tyr Ile Tyr Asp
                325                 330                 335

Phe Ile Lys Lys Phe
                340

<210> SEQ ID NO 3
<211> LENGTH: 1933
<212> TYPE: DNA
<213> ORGANISM: Glycine max
<220> FEATURE:
<221> NAME/KEY: CDS
<222> LOCATION: (271)..(810)
<221> NAME/KEY: CDS
<222> LOCATION: (979)..(1217)
<221> NAME/KEY: CDS
```

-continued

<222> LOCATION: (1367)..(1610)

<400> SEQUENCE: 3

| | | |
|---|---|---|
| aatgaaacat tttatttt tctaatttat ctttaactca tatacaggga agtgaaaaaa | 60 | |
| ataagaaata aatatataaa tgagtgaaaa tataattaat atgaaaaata agagatatta | 120 | |
| taggaaatgc atataatgat tttcgtgaaa tgtaaaatat taaatttcct tttaatatt | 180 | |
| aaaacggcag gttagctcga ggagcctacg gtttggcatt gagtgtgaaa caggctaata | 240 | |

| aatgtgagtg gttcaccgcc gcaacttcaa | atg tgc gag cac tta ctc gtc tca | 294 |
|---|---|---|
| | Met Cys Glu His Leu Leu Val Ser | |
| | 1             5 | |

| ctg tct tgc tat att tgg gtg aga aca cag agg ata gtg gag ttc aac | 342 |
|---|---|
| Leu Ser Cys Tyr Ile Trp Val Arg Thr Gln Arg Ile Val Glu Phe Asn | |
|     10              15              20 | |

| gag atg gag caa ata aag cac aga aca gtt gaa gtg aat ggc ata aaa | 390 |
|---|---|
| Glu Met Glu Gln Ile Lys His Arg Thr Val Glu Val Asn Gly Ile Lys | |
| 25              30              35              40 | |

| atg cat ggt gca gag aaa gga gag ggt cca gtg gtg ttg ttc ctc cac | 438 |
|---|---|
| Met His Gly Ala Glu Lys Gly Glu Gly Pro Val Val Leu Phe Leu His | |
|                 45              50              55 | |

| ggc ttc cct gag ctc tgg tac tca tgg cgc cat cag att ctc tct ctc | 486 |
|---|---|
| Gly Phe Pro Glu Leu Trp Tyr Ser Trp Arg His Gln Ile Leu Ser Leu | |
|             60              65              70 | |

| agc tcc ctc ggc tac cgc gcc gtc gct ccc gat ctc cgt ggc tac ggt | 534 |
|---|---|
| Ser Ser Leu Gly Tyr Arg Ala Val Ala Pro Asp Leu Arg Gly Tyr Gly | |
|         75              80              85 | |

| gac acc gaa gca cca cct tca atc agc agc tac aac tgc ttc cac ata | 582 |
|---|---|
| Asp Thr Glu Ala Pro Pro Ser Ile Ser Ser Tyr Asn Cys Phe His Ile | |
|     90              95              100 | |

| gtg ggt gat ctc gtt gcg ctt att gac tct ctg ggt gtc caa caa gtg | 630 |
|---|---|
| Val Gly Asp Leu Val Ala Leu Ile Asp Ser Leu Gly Val Gln Gln Val | |
| 105             110             115             120 | |

| ttc ctt gtg gct cat gac tgg gga gcc atc ata ggt tgg tat cta tgc | 678 |
|---|---|
| Phe Leu Val Ala His Asp Trp Gly Ala Ile Ile Gly Trp Tyr Leu Cys | |
|                 125             130             135 | |

| atg ttt cgc cct gac aaa gtt aag gcc tat gtc tgc ctc agt gtc cct | 726 |
|---|---|
| Met Phe Arg Pro Asp Lys Val Lys Ala Tyr Val Cys Leu Ser Val Pro | |
|             140             145             150 | |

| ctc ctc cgc aga gac cca aac atc aga acg gtg gat ggc atg cgt gct | 774 |
|---|---|
| Leu Leu Arg Arg Asp Pro Asn Ile Arg Thr Val Asp Gly Met Arg Ala | |
|         155             160             165 | |

| ttg tat gga gac gac tac tat gtc tgc aga ttt cag gtttattaat | 820 |
|---|---|
| Leu Tyr Gly Asp Asp Tyr Tyr Val Cys Arg Phe Gln | |
|     170             175             180 | |

| | |
|---|---|
| taattctctc attttgctta tttttatccc acccttgttt ttctttctct ttctaattaa | 880 |
| ctttgcacga aatttaattt gtttctgtga aatggggtcg gaagattgta gtaccagatg | 940 |
| cgaattattg ttttaaacc gtgtgtgtgt aactgcag aaa cca ggg gaa atg gag | 996 |
|                                          Lys Pro Gly Glu Met Glu | |
|                                                          185 | |

| gct cag atg gct gaa gtt ggc act gag tat gtt ctc gaa aac atc ctt | 1044 |
|---|---|
| Ala Gln Met Ala Glu Val Gly Thr Glu Tyr Val Leu Glu Asn Ile Leu | |
|             190             195             200 | |

| aca act cgc aat cct ggt cct cca att ctt ccc aag gga agg ttt caa | 1092 |
|---|---|
| Thr Thr Arg Asn Pro Gly Pro Pro Ile Leu Pro Lys Gly Arg Phe Gln | |
|         205             210             215 | |

| ttc aat cca gaa atg ccc aac acc ttg ccc tct tgg ctc aca gaa gaa | 1140 |
|---|---|
| Phe Asn Pro Glu Met Pro Asn Thr Leu Pro Ser Trp Leu Thr Glu Glu | |
|     220             225             230 | |

```
gat ctc gcc tat tat gtc tcc aaa ttt gag aaa acc gga ttc act gga    1188
Asp Leu Ala Tyr Tyr Val Ser Lys Phe Glu Lys Thr Gly Phe Thr Gly
235                 240                 245                 250 ccc ttg aac tac tac aga aat ttc aac tt gtaatttctt gattctccgt       1237
Pro Leu Asn Tyr Tyr Arg Asn Phe Asn Leu
                    255                 260 atttgcccgg ataattgtt ttccactgct ctaagttaat gtttctttct tgggaaaata   1297
tttgttcaac atgacgggat cccaataaaa aaagaccatt aattaattaa ttattgtatg  1357 tatttgcag a aat tgg gag ttg acg gca cca tgg aca gga ggg caa atc    1406
           Asn Trp Glu Leu Thr Ala Pro Trp Thr Gly Gly Gln Ile
                            265                 270 aag gtg ccc gta aaa tac ata aca ggt gag ttg gac atg gta tac aac    1454
Lys Val Pro Val Lys Tyr Ile Thr Gly Glu Leu Asp Met Val Tyr Asn
    275                 280                 285 tcg ctg aac ttg aag gag tat atc cac ggc gga ggg ttc aag caa gat    1502
Ser Leu Asn Leu Lys Glu Tyr Ile His Gly Gly Gly Phe Lys Gln Asp
290                 295                 300                 305 gtg cca aat tta gaa caa gtg att gtg cag aaa gga gtg gct cac ttc    1550
Val Pro Asn Leu Glu Gln Val Ile Val Gln Lys Gly Val Ala His Phe
                310                 315                 320 aat aat caa gaa gca gca gag gaa atc gat aat tac ata tac gat ttt    1598
Asn Asn Gln Glu Ala Ala Glu Glu Ile Asp Asn Tyr Ile Tyr Asp Phe
                325                 330                 335 atc aac aag ttc tgatcttgtc caaaaacgaa ttcaaccaga tataaagtcg        1650
Ile Asn Lys Phe
            340 cagctgaagt gaaagggtgt tataattgcg cttttgtttt gatatttaag gtatcgagat  1710 cttttttatg ggcaggattc atcaactgca gaaaacctcc ataccatcaa ccttcctatg  1770 cttgtttgta ttaattaact gataataata ctgtatggtt tggtacttgc taaataaact  1830 tagtcttgtc atgcaaatgg tatatcttaa aaaatgtttt gaaatatgtg tatttggaac  1890 taagcttcaa tgcgtgtgtg tatatctcga cataatctcg tag                    1933
```

<210> SEQ ID NO 4
<211> LENGTH: 341
<212> TYPE: PRT
<213> ORGANISM: Glycine max

<400> SEQUENCE: 4

```
Met Cys Glu His Leu Leu Val Ser Leu Ser Cys Tyr Ile Trp Val Arg
1               5                   10                  15

Thr Gln Arg Ile Val Glu Phe Asn Glu Met Glu Gln Ile Lys His Arg
                20                  25                  30

Thr Val Glu Val Asn Gly Ile Lys Met His Gly Ala Glu Lys Gly Glu
            35                  40                  45

Gly Pro Val Val Leu Phe Leu His Gly Phe Pro Glu Leu Trp Tyr Ser
        50                  55                  60

Trp Arg His Gln Ile Leu Ser Leu Ser Ser Leu Gly Tyr Arg Ala Val
65                  70                  75                  80

Ala Pro Asp Leu Arg Gly Tyr Gly Asp Thr Glu Ala Pro Pro Ser Ile
                85                  90                  95

Ser Ser Tyr Asn Cys Phe His Ile Val Gly Asp Leu Val Ala Leu Ile
            100                 105                 110

Asp Ser Leu Gly Val Gln Gln Val Phe Leu Val Ala His Asp Trp Gly
        115                 120                 125
```

Ala Ile Ile Gly Trp Tyr Leu Cys Met Phe Arg Pro Asp Lys Val Lys
        130                 135                 140

Ala Tyr Val Cys Leu Ser Val Pro Leu Leu Arg Arg Asp Pro Asn Ile
145                 150                 155                 160

Arg Thr Val Asp Gly Met Arg Ala Leu Tyr Gly Asp Tyr Tyr Val
                165                 170                 175

Cys Arg Phe Gln Lys Pro Gly Glu Met Glu Ala Gln Met Ala Glu Val
            180                 185                 190

Gly Thr Glu Tyr Val Leu Glu Asn Ile Leu Thr Thr Arg Asn Pro Gly
        195                 200                 205

Pro Pro Ile Leu Pro Lys Gly Arg Phe Gln Phe Asn Pro Glu Met Pro
    210                 215                 220

Asn Thr Leu Pro Ser Trp Leu Thr Glu Glu Asp Leu Ala Tyr Tyr Val
225                 230                 235                 240

Ser Lys Phe Glu Lys Thr Gly Phe Thr Gly Pro Leu Asn Tyr Tyr Arg
                245                 250                 255

Asn Phe Asn Leu Asn Trp Glu Leu Thr Ala Pro Trp Thr Gly Gly Gln
            260                 265                 270

Ile Lys Val Pro Val Lys Tyr Ile Thr Gly Glu Leu Asp Met Val Tyr
        275                 280                 285

Asn Ser Leu Asn Leu Lys Glu Tyr Ile His Gly Gly Phe Lys Gln
    290                 295                 300

Asp Val Pro Asn Leu Glu Gln Val Ile Val Gln Lys Gly Val Ala His
305                 310                 315                 320

Phe Asn Asn Gln Glu Ala Ala Glu Glu Ile Asp Asn Tyr Ile Tyr Asp
                325                 330                 335

Phe Ile Asn Lys Phe
            340

<210> SEQ ID NO 5
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: ()..()
<223> OTHER INFORMATION: N is A, G, C, or T

<400> SEQUENCE: 5
ggcatytcng grttraaytg raa                                              23

<210> SEQ ID NO 6
<211> LENGTH: 32
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

<400> SEQUENCE: 6
atatacatat ggagcaaata aagcacagaa ca                                    32

<210> SEQ ID NO 7
<211> LENGTH: 34
<212> TYPE: DNA

-continued

```
<213> ORGANISM: Artificial Sequence
<220> FEATURE:
<221> NAME/KEY: misc_feature
<222> LOCATION: ()..()
<223> OTHER INFORMATION: Description of Artificial Sequence:primer

<400> SEQUENCE: 7
ggttgaattc gttttggac aagatcagaa cttc                                    34
```